(12) United States Patent
Bacher et al.

(10) Patent No.: US 6,540,737 B2
(45) Date of Patent: Apr. 1, 2003

(54) HANDLE FOR A MEDICAL INSTRUMENT

(75) Inventors: Uwe Bacher, Tuttlingen (DE); Alfred Cuschieri, St. Andrews Fife (GB); Timothy Graham Frank, Newport-On-Tay Fife (GB)

(73) Assignee: Karl Storz GmbH & Co. KG (DE)

( * ) Notice: Subject to any disclaimer, the term of this patent is extended or adjusted under 35 U.S.C. 154(b) by 167 days.

(21) Appl. No.: 09/733,144

(22) Filed: Dec. 8, 2000

(65) Prior Publication Data
US 2001/0027312 A1 Oct. 4, 2001

Related U.S. Application Data

(63) Continuation of application No. PCT/EP99/09280, filed on Nov. 29, 1999.

(30) Foreign Application Priority Data

Dec. 28, 1998 (DE) .......................................... 198 60 444

(51) Int. Cl.[7] .............................................. A61B 17/00
(52) U.S. Cl. ........................................ 606/1; 600/131
(58) Field of Search ............................... 600/131; 606/1, 606/167, 205; 81/177.1, 177.8, 489

(56) References Cited

U.S. PATENT DOCUMENTS 5,352,237 A  * 10/1994 Rodak et al. ............... 600/104
5,483,952 A  *  1/1996 Aranyi ........................ 600/131
5,556,416 A  *  9/1996 Clark et al. ................. 600/563
5,626,608 A  *  5/1997 Cuny et al. ................. 600/131

* cited by examiner

Primary Examiner—Linda C. M. Dvorak
Assistant Examiner—Jocelyn Ram
(74) Attorney, Agent, or Firm—St. Onge Steward Johnston & Reens LLC

(57) ABSTRACT

A handle is provided for a medical instrument having a tubular shaft. The handle comprises at least one movable grip element as well as a coupling portion through which the tubular shaft is connected or can be connected to the handle. The movable grip element is or can be connected to a force transmission element axially movable in the direction of a longitudinal axis of the tubular shaft. Motion of the at least one movable is translated into an axial motion of the force transmission element. The coupling portion is pivotal and lockable relative to a handle axis about a pivot axis running transversely to the longitudinal axis of the tubular shaft. A control element formed as a dual-arm lever is provided whose one lever arm is connected to the movable grip element and whose other lever arm is connected to the force transmission element, such that motion of the movable grip element causes rotation of the control element, which is translated into an axial movement of the force transmission element.

17 Claims, 5 Drawing Sheets

HANDLE FOR A MEDICAL INSTRUMENT

CROSS-REFERENCE TO PENDING APPLICATION

This application is a continuation of pending International Application PCT/EP99/09280 filed on Nov. 29, 1999, which designates the United States.

BACKGROUND OF THE INVENTION

The invention relates to a medical instrument having a tubular shaft, comprising a movable grip element and a coupling portion through which the tubular shaft is connected or can be connected to the tubular shaft. The movable grip element is connected or can be connected to a force transmission element axially movable in the direction of the longitudinal axis of the tubular shaft. Motion of the at least one movable grip element translates into axial motion of the force transmission element.

A handle of this type is disclosed for example in the German company brochure of Karl Storz GmbH & CO., Tuttlingen, "KARL STORZ—ENDOSKOPE", Vol. "Endoskopische Chirurgie", 2nd Edition Jan. 1994, page DGC 5/1A.

Tubular shaft instruments are used in various types of operative procedures on the human and animal body, in particular for minimally invasive surgery. Such instruments can be formed as pinchers, for example preparation and grasping forceps, forceps for separating or cutting tissue as well as for stamping or punching and the like. The instruments are distinguished according to their various functions by the corresponding configuration of the tools at their distal end. Cutting tools, grasping tools or stamping or punching tools can be provided at the distal end of the tubular shaft, where the instrument comprises at least one movable tool, for example in the form of a jaw part. However, two movable tools can be provided at the distal end of such instruments.

Tubular shaft instruments comprise a handle at the proximal end of the shaft for actuating the at least one movable tool. The shaft of the instrument is normally connected to a coupling portion of the handle in non-releasable or releasable manner. In addition, the handle comprises at least one movable grip element for the purpose of actuating the at least one movable tool at the distal end. To actuate the at least one movable tool at the distal end of the tubular shaft, the at least one movable grip element of the handle is connected with the at least one movable tool via a force transmission element axially movable in the direction of the longitudinal axis of the shaft, for example a push or pull rod. Consequently, movement of the movable grip element, for example a pivotal or axial movement, is translated into axial relative motion of the force transmission element with respect to the shaft and finally into motion of the movable tool.

A handle of the mentioned type is known in various configurations. Normally, the handle comprises a second grip element which is either fixed to be immovable or is also movable. Such a handle can also be formed in the manner of a scissors handle, where both grip elements extend to the side from the shaft of the instrument, as is the case in the company brochure mentioned above. In this type of handle the at least one movable grip element is pivotally connected with the other grip element about a pivot axis running transversely to the longitudinal axis of the shaft. In the sense of the present invention, the handle however can also be formed as a type of pistol grip element, so that the handle can be held as a bar grip element in the fist of one hand.

Common to all of these known handles is that the handle in the condition of being connected to the shaft has a fixed angular position with respect to the shaft, i.e. the handle axis and the longitudinal axis of the shaft form a fixed angle to one another. A handle having a fixed angular disposition with respect to the shaft axis is however not always adapted with respect to its handling properties to the needs of the physician operating the instrument. Depending on the habits of different physicians, different grip element positions are desired for the same type of handle. To always have the optimal ergonomic handle available, it would therefore be necessary to provide a set of several handles for each type of handle, which would then allow each different angular position with respect to the shaft. Thus each physician could then select the most ergonomic handle for himself. In case the handle is not exchangeable, this would mean that a complete set of such instruments would need to be provided for each tubular shaft instrument with handles having differing angles.

In certain cases, it can also be desirable or necessary that the handle of the same instrument be able to undertake different positions during an operative procedure, to therefore allow the most comfortable or convenient positioning of the handle for the operative procedure being carried out. With the known handles, which would be present as a complete set, this would mean that the handle would have to be exchanged several times during the operation or if the handles are not removable, even the entire instrument would have to be exchanged, which would prolong the operation time.

The known handles therefore have drawbacks with respect to their ergonomic properties.

From DE 196 32 135 A, a medical instrument is known which comprises a tubular shaft. The shaft can be pushed with its guide member and its screw member via a sliding member and a rotatable tappet. The latter is moved by the pressure of an end-surface of an eccentric disc when it rotates about a point. An eccentric disc is rotatably mounted between an upper baring disc and a lower baring disc with a screw. The handle of this known instrument can be pivoted relative to the tubular shaft. However, the mechanism of the force transmission from the movable grip element to the shaft which is the force transmission element of this known instrument, is disadvantageous because of the enhanced friction between the outer surface of the eccentric disc and the tappet.

An object of the present invention is therefore to provide an improved handle of the mentioned type, such that the handle allows ergonomic work with the tubular shaft instrument, without having to exchange the handle or even the entire instrument, wherein the force transmission mechanism between the movable grip element and the force transmission element is also improved.

SUMMARY OF THE INVENTION

This object is achieved by a handle for a medical instrument having a tubular shaft, comprising:
at least one movable grip element for being connected to a force transmission element axially movable in direction of a longitudinal axis of said tubular shaft to transfer motion of said at least one movable grip element into an axial motion of said force transmission element,
a coupling portion for connecting said tubular shaft with said handle,
said coupling portion being pivotal and lockable relative to a handle axis about a pivot axis running transversely to said longitudinal axis of said tubular shaft, a control element formed as a double-arm lever, a first lever arm of which being connected to said at least one movable grip element, and a second lever arm of which being connected to said force transmission element, such that motion of said movable grip element causes a rotation of said control element, wherein said control element translates said rotation into an axial movement of said force transmission element.

Thus according to the invention, the coupling portion, which couples or can couple the handle to the tubular shaft, is configured to be pivotal and lockable, where it is achieved that the handle can be set at different angular positions with respect to the shaft. The adjusted angular position of the handle can be locked to rigidly interconnect the shaft with the handle, thereafter the tubular shaft instrument can then be employed in an operative procedure. With the pivotal configuration of the coupling portion, the physician can adjust the ergonomic angular position between the handle and the shaft, which is optimal for himself, without having to exchange the handle or the entire instrument. The handle according to the present invention is therefore substantially improved with respect to ergonomics.

When adjusting the handle axis with respect to the longitudinal axis of the shaft, the problem arises that the force transmission element must be so connected to the movable grip element that the motion of the movable grip element at any angular position translates into axial movement of the force transmission element. The force transmission element in the conventional handles, which normally is configured as a push or pull rod, is directly connected to the movable grip element at its proximal end. This type of connection of the force transmission element however cannot be maintained when the handle can be disposed at different angles with respect to the shaft.

This would mean that the force transmission element would also have to be bent or angled in the region of the pivotal axis of the coupling portion, where a compensation for the length of the force transmission element would also have to be provided. The use of a flexible force transmission element would also have to be provided. The use of a flexible force transmission element, which could account for the angled region would be disadvantageous, because greater friction would occur in the region of the angled components.

According to the present invention, a force transmission mechanism is provided between the movable grip element and the force transmission element, by which a control element is disposed between these two parts whose one lever arm is connected with the movable grip element and whose other lever arm is connected to the force transmission element. The movable grip element thus engages with the one lever arm of the control element and the force transmission element engages with the other lever arm of the control element. Actuating the movable grip element causes rotation of the control element, which is translated by the control element via the second lever arm into an axial movement of the force transmission element.

This type of transmission mechanics from the movable grip element to the force transmission element enable force transmission independent of the respectively adjusted pivot position of the coupling portion and thus the respectively adjusted pivot position of the handle. Thus the further advantage is achieved that the force transmission ratio can be selected to be the same in any pivot position of the handle with respect to the shaft. It is then avoided that differing forces are exerted by the physician when actuating the tool at the distal end of the shaft depending on the pivot position of the handle.

In a preferred embodiment, the pivot axis of the coupling portion coincides with a pivot axis of the control element.

A simple construction of the force transmission mechanism is achieved by this feature, because only a single pivotal mounting need be provided for the coupling portion and for the control element.

In a further preferred embodiment, the control element is connected to the coupling portion and rotates with the same when pivoting the coupling portion to set the angular position of the handle, where the connection to the movable grip element for pivoting the control element is releasable and after pivoting it is re-established.

The feature has the advantage that when the coupling portion is pivoted to adjust the handle at a different angle with respect to the longitudinal axis of the shaft, the control element is pivoted at the same time so that the position of the control element is adapted to the newly adjusted angular position of the handle. This avoids any change in the force transmission without having to additionally manipulate the control element.

In a further preferred embodiment, the at least one movable grip element is connected to a first lever arm of a further double-arm lever, whose other lever arm is connected to the second lever arm of the control element, where a pivot axis of the lever coincides with the pivot axis of the coupling portion.

This achieves a kinematically favorable force transmission from the movable grip element to the control element, which allows high force transmission at all angular positions.

Preferably, the second lever arm of the lever is interconnected to the control element via a pin, where several holes are provided in the control element arranged at a circular section thereof, through which, depending on the pivot position of the coupling portion, the pin is engageable with one of the holes.

This feature is of particular advantage, especially with the above-mentioned feature that the control element being pivotable together with the coupling portion, because the mentioned lever can be easily disengaged in any adjusted pivot position of the coupling portion before pivoting the control element and can be re-engaged after pivoting.

In a further preferred embodiment, the coupling portion is lockable by means of a locking mechanism in several pivot positions in an angular range of up to about 240° with respect to the longitudinal axis of the tubular shaft.

According to this feature, the handle can be pivoted in an angular range between about −120° and about +120° and be locked in at least two, preferably however a plurality of pivot positions. The ergonomics of the handle with its angular position with respect to the shaft can be adjusted within a large angular range at the desire of the physician. The pivot range however can also be smaller, for example between about −90° and +90° or between about 0° and +120° to name a few examples.

Preferably, the locking mechanism comprises a locking nose engageable with recesses in the coupling portion. The locking mechanism further comprises a button so that the locking nose is disengageable with the respective recess when depressing the button.

This type of locking and disengaging the coupling portion advantageously leads to a simple operation of the pivoting and locking of the handle.

In a further preferred embodiment of the invention, the pin is connected to the button and is disengageable from the respective hole in the control element by depressing the button.

With this feature, both the construction of the handle is simplified and the manipulation operations are improved, because only one button need be actuated to unlock both the coupling portion and the control element for pivoting.

In a further preferred embodiment, the second lever arm of the control element comprises a recess formed as a guide slot in which a pin connected to the force transmission element is axially guided.

With this configuration of the control element and the correspondingly formed guide slot, a translation of the pivotal movement of the control element into an axial movement of the force transmission element is achieved in constructively very simple manner.

Alternatively, the force transmission element can also be connected to the control element via a lever.

In this configuration, the lever is then journaled to one end of the control element, where a pivoting of the control element then rotates the lever and the rotation of the lever then causes translational motion of the force transmission element in the manner of a piston rod.

In a further preferred embodiment, the coupling portion comprises a receptor for a proximal end of the force transmission element, where the receptor is axially movable and connected to the pin or to the lever.

In this configuration, the force transmission element is not connected directly to the control element, but through a receptor lying outside of the control element. The advantage is that the connection between the force transmission element and the control element is particularly simple to produce. In addition, this configuration allows the possibility of connecting the force transmission element releasably with the handle.

Preferably, the receptor comprises a locking mechanism for releasably connecting the force transmission element to the coupling portion.

The advantage is that the force transmission element can be removed from the coupling portion and therefore from the handle, where the force transmission element after removal from the handle can be more easily cleaned.

In a further preferred embodiment, the coupling portion comprises a receptor for the tubular shaft for releasably connecting the shaft with the coupling portion.

The advantage is that the shaft can also be removed from the handle, where the ability to clean such an instrument with a tubular shaft is further improved.

An instrument comprising a tubular shaft, at least one movable tool at the distal end of the shaft and a force transmission element arranged to be axially movable in the tubular shaft for actuating the at least one movable tool, is advantageously equipped with a handle according to the invention having one or more of the above features.

Preferably, the tubular shaft and/or the force transmission element is releasably connected to the handle and/or the force transmission element is releasably connected to the tubular shaft. With the releasable configuration of the shaft and the force transmission element, the instrument can be disassembled into the shaft, the force transmission element and the handle, where each of the assemblies can be better cleaned.

Further advantages result from the following description and the appended drawings. It will be understood that the above-mentioned features and those to be described below are applicable not only in the given combinations, but also in other combinations or when taken alone without departing from the scope of the present invention.

An embodiment of the invention is described below in conjunction with the drawings.

DETAILED DESCRIPTION OF A PREFERRED EMBODIMENT

Figure 1:
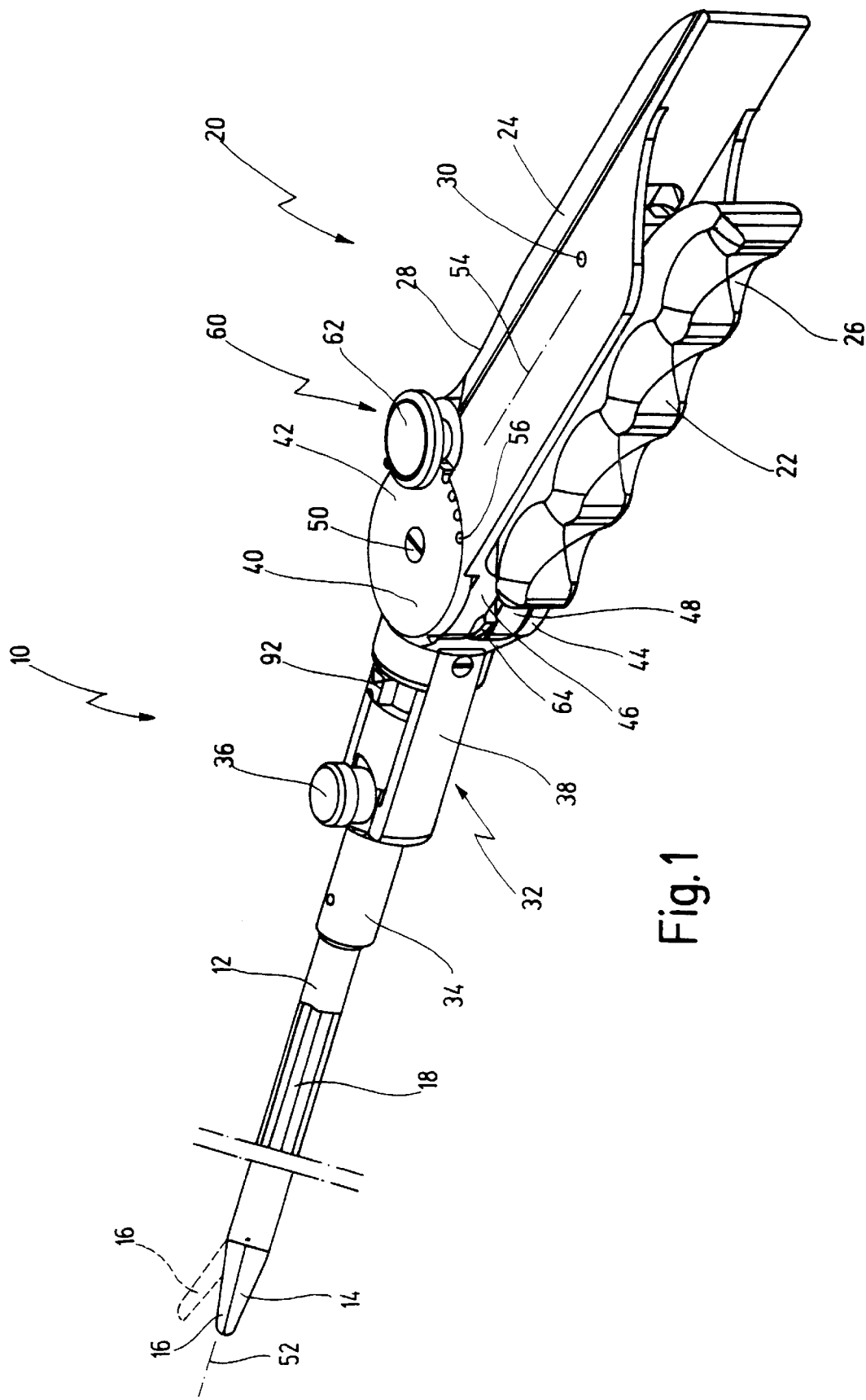
FIG. 1 shows a perspective total view of an instrument with a tubular shaft comprising a handle according to the present invention.

A medical instrument having a tubular shaft is illustrated in FIG. 1 and designated generally with the numeral 10. The instrument is intended for operative procedures in the human and animal body for preparing tissue.

The instrument 10 comprises an elongated tubular shaft 12 having a first tool 14 and a second tool 16 arranged at its distal end. The second tool 16 is formed to be movable relative to the first tool 14 and is pivotally connected to the shaft 12 for this purpose. The first tool 14 and the second tool 16 are formed as jaw parts having a cutting function for removing tissue.

Figure 2:
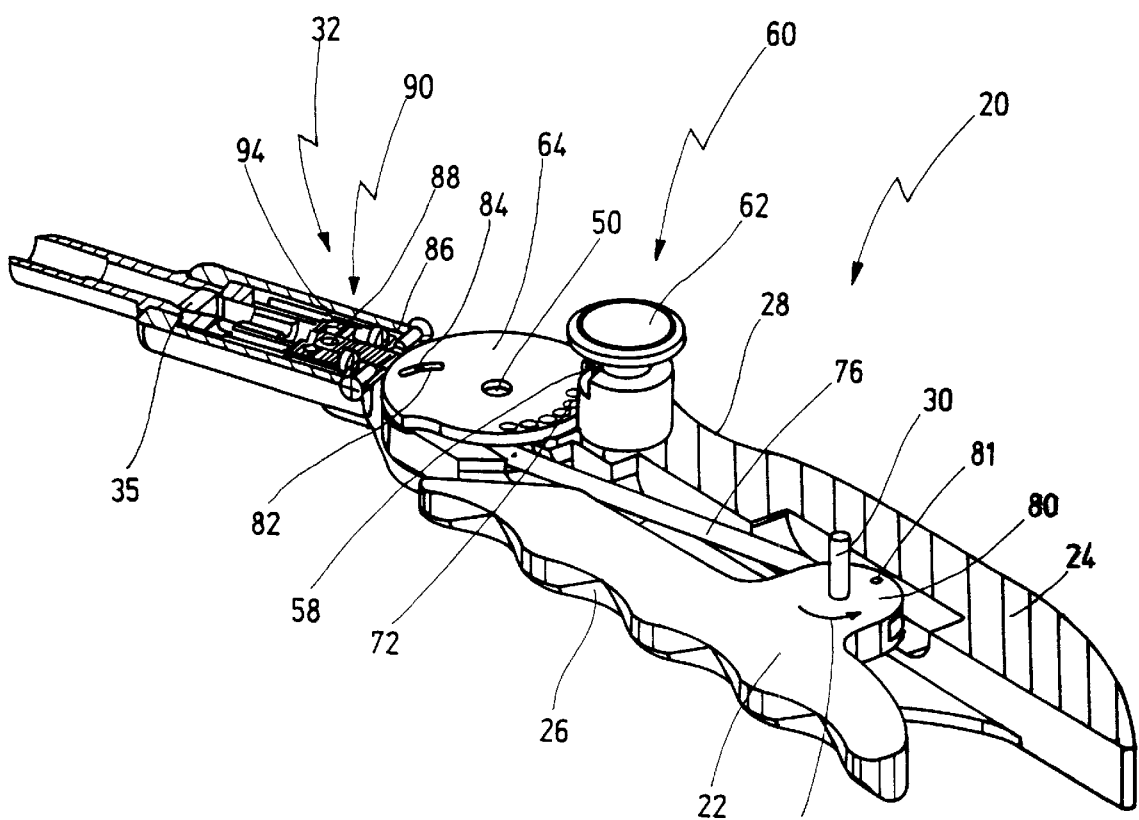
FIG. 2 shows a perspective view in partial cross-section of the handle in FIG. 1, where parts have been left out.
Figure 3:
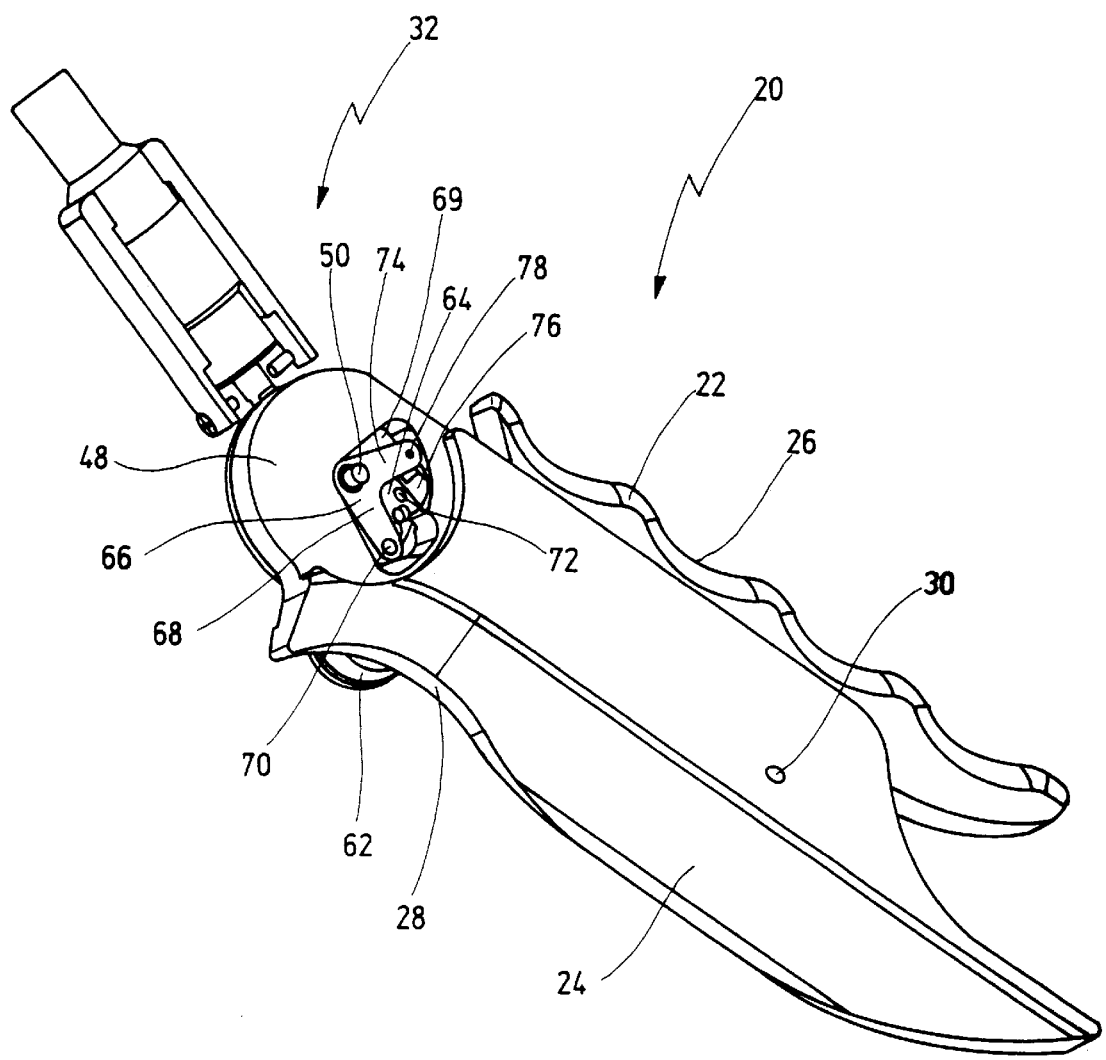
FIG. 3 shows a perspective view of the side of the handle hidden in FIGS. 1 and 2 with parts being left out.
Figure 4:
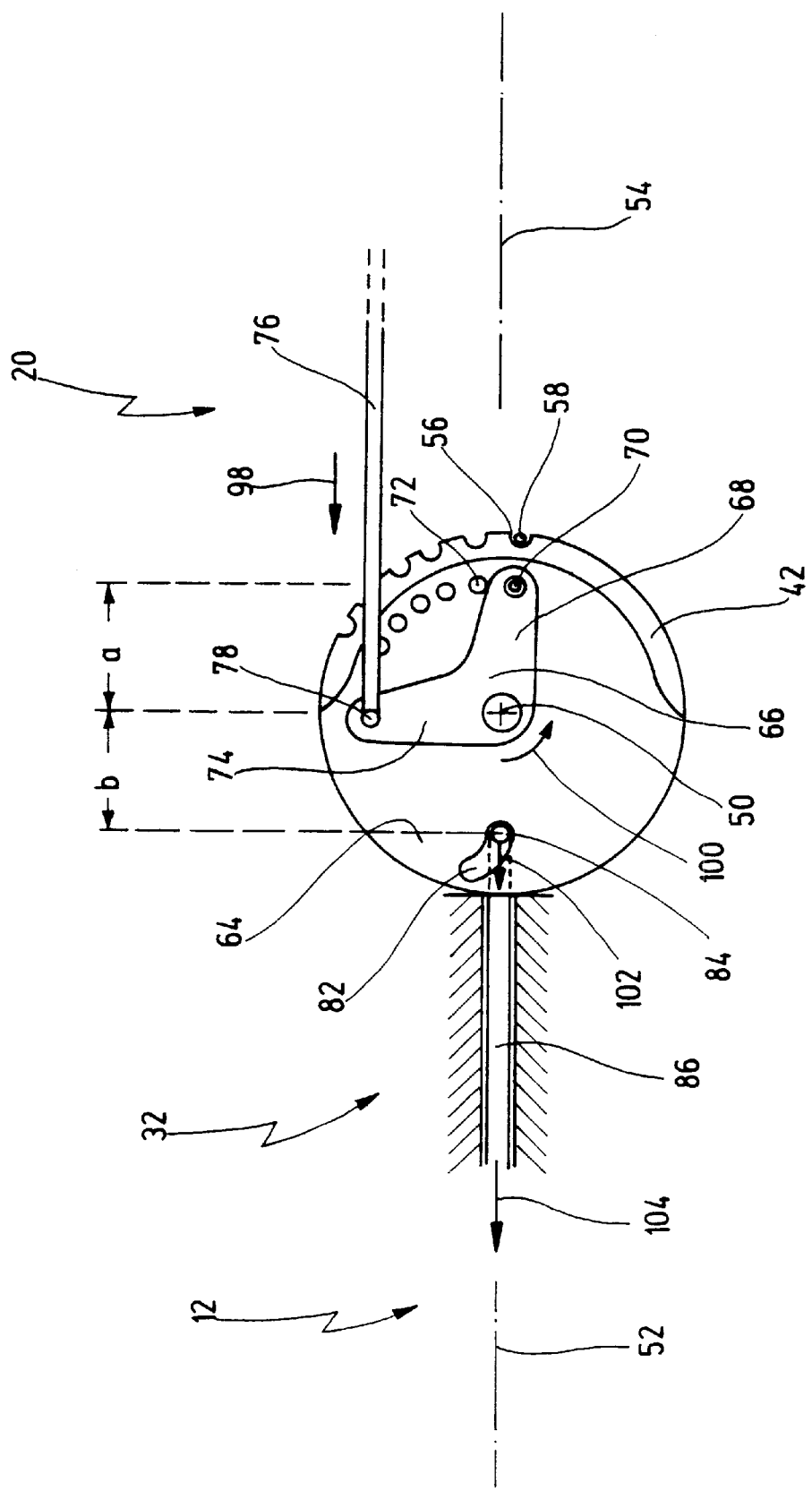
FIG. 4 shows a schematic diagram of the principle of the force transmission mechanism in a first operation position, where the handle axis forms an angle of about 0° with the longitudinal axis of the shaft.
Figure 5:
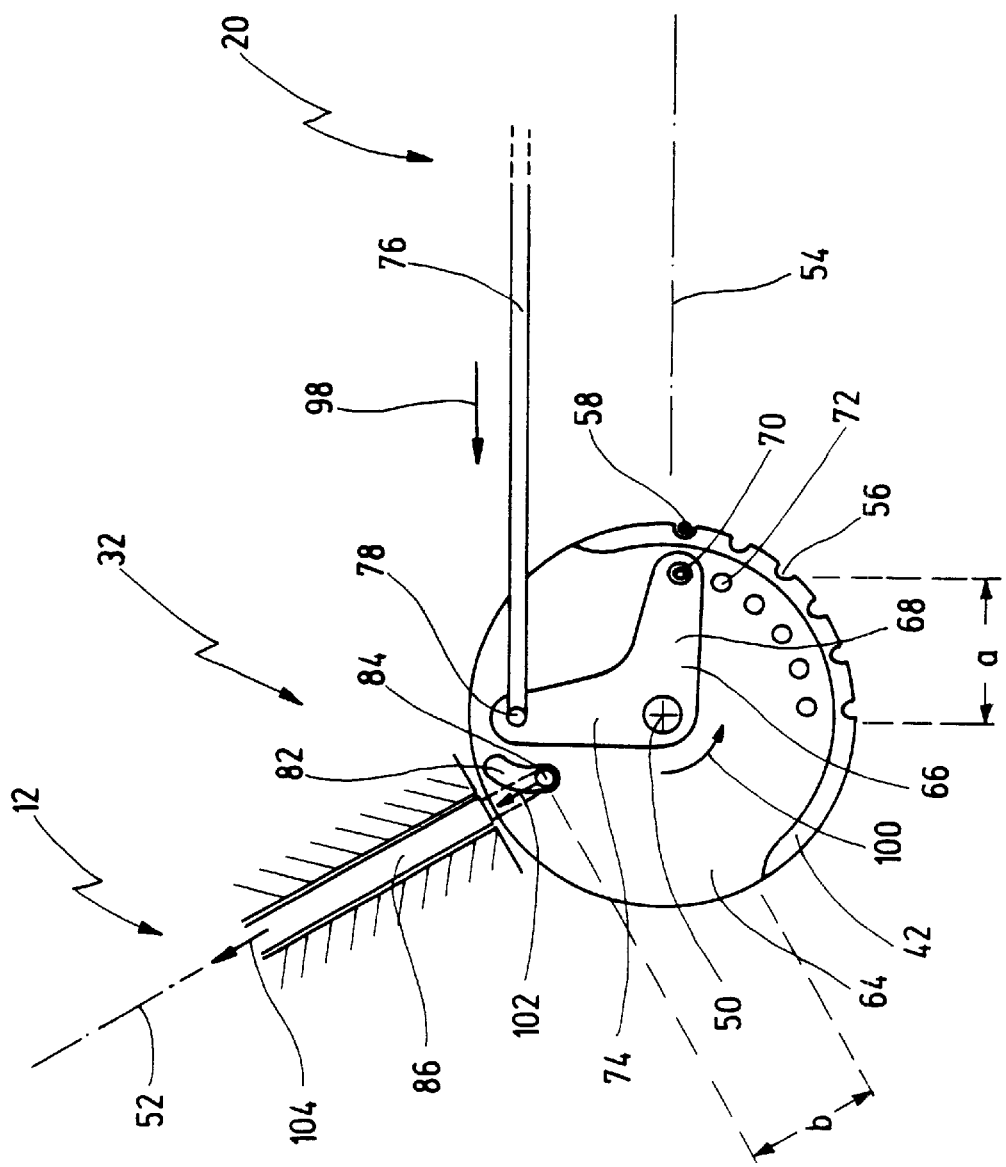
FIG. 5 shows a schematic illustration of the principle of the force transmission mechanism in an operation position where the handle axis forms an angle of about 60° with the longitudinal axis of the shaft.

The instrument 10 comprises a handle 20 at the proximal end of the shaft 12, which is described in more detail below in conjunction with FIG. 1 as well as FIGS. 2 and 3. Furthermore, FIGS. 4 and 5 show diagrams of the principle of the force transmission mechanism of the handle 20. As seen in FIGS. 1 to 3, the handle 20 comprises a movable grip element 22 and a non-movable grip element 24. The movable grip element 22 has four finger wells 26 for the index, middle, ring and little finger. The non-movable grip element 24 correspondingly comprises a thumb well 28 for the thumb. The movable grip element 22 is pivotally connected to the non-movable grip element 24 about a pivot axis 30.

The handle 20 further comprises a coupling portion 32 at its distal end, through which a shaft 12 is connected or can be connected to the handle 20. For this purpose, a proximal end of the shaft 12 is inserted into a distal tube 34 of the coupling portion 32 and locked to the coupling portion 32 via a locking mechanism at 35 (see FIG. 2). The locking mechanism is releasable by means of a button 36 to remove the shaft 12 from the coupling portion 32.

The tube 34 is rigidly connected to a proximal end section 40 of the coupling portion 32 through a forked cradle 38 which forms a middle section of the coupling portion 32. The end portion 40 is also formed as a forked member comprising two substantially round plates 42, 44. The fork-shape end section 40, i.e. more precisely the plates 42 and 44 are seated respectively on forked extensions 46, 48 of the non-movable grip element 24. In this manner, the coupling portion 32 is connected to the non-movable grip element 24.

The special feature of the coupling portion 32 is now that the end section 40 of the coupling portion 32 is pivotal about a pivot axis 50, which runs transversely to a longitudinal axis 52 of the shaft 12, in the present embodiment perpendicular to the longitudinal axis 52. In this manner, the handle 20 can be disposed at different angles with respect to the shaft 12. A handle axis 54 of the handle 20, selected here to be about the center axis of the handle 20, can therefore take on various angular positions with respect to the longitudinal axis 52 of the shaft 12, namely angular positions between about 0° (see FIG. 4) and about 60° (see FIG. 5). In the illustrated embodiment, the maximal angular adjustability between the handle axis 54 and the longitudinal axis 52 of the shaft 12 is therefore about 60°. However, it can be appropriate for other instruments having a tubular shaft, which makes use of the handle 20, to provide the coupling portion to be pivotal and lockable over an entire angular range of about 240°, for example between −120° and +120°.

The coupling portion 32 is lockable in several angular positions, in the present embodiment in six different angular positions. For this purpose, plate 42 of the end section 40 comprises peripheral recesses 56 in the form of notches into which a locking nose 58 can engage.

The recesses 56 and the nose 58 are parts of the locking mechanism 60, which additionally comprises a button 62 rigidly connected to the locking nose 58. By depressing the button 62, the locking nose 58 is disengaged from the recess 56 in which the nose is presently located, after which the coupling portion 32 can be pivoted about the pivot axis 50 with respect to the grip elements 22, 24. After releasing the button 62, which is secured to the non-movable grip element 24, the nose 58 automatically engages the recess 56 at the corresponding pivot position of the nose 58. In this manner, the coupling portion 32 is locked and fixed against rotation with the non-movable grip element 24 and the movable grip element 22.

The button 62 is preferably spring-mounted, so that it is actuated against a spring force and automatically returns to its starting position after release of the button 62.

The handle 20 further comprises a force transmission mechanism for transmitting force from the movable grip element 22 to the force transmission element 18 as will be discussed in detail in the following. The force transmission mechanism comprises a control element 64. The control element 64 is arranged between the plates 42, 44 of the fork-shaped end section 40 of the coupling portion 32.

The control element 64 is provided in the form of a substantially round plate, which is pivotally mounted about the same pivot axis 50 as the coupling portion 32. The pivot axis 50 is formed by a pin passing through the plate 42, the distal forked extensions 46, 48 of the non-movable grip element 24, the control elements 64 and the plate 44. The pin is provided in the form of a screw, where the screw holds the mentioned parts together.

The control element 64 is rotatable relative to the plates 42, 44 of the fork-shaped end section 40 of the coupling portion 32 about the pivot axis 50. The control element 64 is arranged between the distal forked extensions 46, 48 of the non-movable grip element 24. The control element 64 is further formed as a double-arm lever, as will be described below.

The control element 64 interacts with a double-arm lever 66, which is received in a recess 69. The recess 69 is located on a side of the forked extension 48 of the non-movable grip element 24, which opposes the control element 64. The lever 66 is pivotally mounted in the recess 69, namely about the same pivot axis 50 as the coupling portion 32 and the control element 64, i.e. the above-mentioned screw also passes through the lever 66.

The lever 66 comprises a first lever arm 68 frictionally connected to the control element 64 with a pin 70. The pin 70 engages in a hole at the outer end of the first lever arm 68 of the lever 66 and also in one of the several holes 72, which are provided at the periphery in the control element 64 distributed about a circular section. The number of holes 72 is equal to the number of recesses 56 in the fork-shaped end section 40, more precisely in the plate 42.

The pin 70 is also connected to the button 62 of the locking mechanism 60, namely such that when depressing the button 62, the pin 70 remains engaged with the first lever arm 68, however disengages with the corresponding hole 72 in which it was previously engaged. Thus when depressing the button 62, both the coupling portion 32 and also the control element 64 connected to the coupling portion 32, to be described below, are commonly pivoted about the pivot axis 50, although the lever 66 does not participate in the pivot movement. In addition, the pin 70 is pivotally mounted to the button to be able to follow the rotation of the lever 66.

The lever 66 is formed as an angle and comprises a second lever arm 74 connected to the movable grip element 22 via a coupling rod 76, which is journaled at 78 to the second lever. arm 74. The coupling rod 76 on the other hand is journaled to a projection 80 of the movable grip element 22 at a journal point 81 spaced apart from the pivot axis 30.

The control element 64 comprises a recess 82 formed as a guide slot in a region opposite to the holes 72. The guide slot formed by the recess has a curvature as illustrated in FIGS. 4 and 5. A pin 84 engages in the recess 82, which is axially movable and is guided in the recess 82. The pin 84 is located at the proximal end of a rod-shaped element 86 axially shiftable in the coupling portion 32. The distal end of the element 86 comprises a receptor 88 in the form of a ball socket in which a proximal end of the force transmission element 18 is arranged (not shown in FIG. 2). The proximal end of the force transmission element 18 is releasably secured in the receptor 88 of the coupling portion 32 by means of a locking mechanism 90 having a button 92.

The rod-shaped element 86 and thus the receptor 88 are biased in the proximal direction by a compression spring (not shown) disposed in a spring seat 94.

The function of the handle 20 will now be described, more precisely the force transmission mechanism from the movable grip element 22 to the force transmission element 18. A first operation position of the handle 20 is illustrated in FIG. 4, where the handle axis 54 is aligned with the longitudinal axis 52 of the shaft 12. In operational condition, the nose 58 of the locking mechanism 60 is engaged in the corresponding recess 56 of the plate 42 of the forked end section 40 of the coupling portion 32, so that the handle 20 is rigidly connected to the shaft 12, i.e. secured against rotation. In addition, the pin 70 is disposed in the corresponding hole 72 of the control element 64, so that the lever 66, more precisely the first lever arm 68 is connected to the control element 64.

When the movable grip element 22 is now pivoted about the pivot axis 30 in the direction of the arrow 96 in FIG. 2, the coupling rod 76 shown in FIG. 4 is shifted axially in the distal direction indicated by the arrow 98. The coupling rod 76 engages with the journal point 78 at its other end to the second lever arm 74 of the lever 66, so that the lever 66 about the pivot axis 50 as shown by the arrow 100 in FIG. 4. The first lever arm 68 integrally formed with the second lever arm 74 translates the pivot movement of the lever 66 into a rotation of the control element 64 in the same direction, i.e. also in the direction of the arrow 100.

The distance between the pin 70 or the hole 72 and the pivot axis 50 thus forms a first lever arm a) of a control element 64. A second lever arm b) of the control element 64 is defined by the distance between the pivot axis 50 and the recess 82 in the control element 64.

By pivoting the control element 64 about the pivot axis 50, the pin 84 in the recess 82 formed as a guide slot is urged axially in the direction of the arrow 102, whereby also the rod-shaped element 86 and with it the force transmission element 18 is shifted in distal direction as indicated by the arrow 104, such that the movable jaw part 16 is set in motion. The rotation of the control element 64 about the pivot axis 50, which corresponds to a small angle of about 5 to 10°, is accordingly translated into an axial movement of the force transmission element 18. During this rotation of the control element 64 caused by actuating the movable grip element 22, the coupling portion 32 remains fixed with respect to the pivot axis 50, i.e. the coupling portion 32 does not rotate. When releasing the movable grip element 22, the above movements automatically occur in reverse direction, which is the result of the spring biasing of the rod-shaped element 86 in the proximal direction.

Instead of the recess 82 formed as a guide slot and the pin 84 guided in the recess 82, the connection between the force transmission element 18 and the control element 64 can also be accomplished by a lever (not shown) whose one end is journaled to the control element 64 and its other end connected to the receptor 88. A rotation of the control element 64 then displaces the first end of the lever, whereby the other end connected to the receptor 88 is shifted axially as a type of piston rod, i.e. a translational movement is generated. Should the handle 20 now be placed in another angular position with respect to the shaft 12, the button 62 of the locking mechanism 60 is depressed, where the nose 58 is disengaged with the recess 56 in the plate 42 of the coupling portion 32 and the pin 70 is disengaged with. the hole 72 and the control element 64. When the button 62 is depressed, the movable grip element 22 together with the non-movable grip element 24 can be displaced to the desired angle with respect to the shaft 12.

A maximum angular position of the shaft 12 with respect to the handle 20 is shown in FIG. 5, where the longitudinal axis 52 of the shaft 12 has an angle of about 60° with respect to the handle axis 54 of the handle 20. After releasing the button 62, the nose 58 and the end 70 automatically engage in the recess 56 or the hole 72 as mentioned above.

As can be taken from FIG. 5, the disposition of the. lever 66 with respect to the pivot axis 50 has not changed. However, the control element 64 and the coupling portion 32 have rotated commonly about the pivot axis 50. When the grip element 22 is now pivoted about the pivot axis 30 in the direction of the arrow 96 shown in FIG. 2, this again causes axial movement of the coupling rod 76. This in turn causes a rotation of the lever 66 about the pivot axis 50 as shown by the arrow 100 and at the same time a rotation of the control element 64 also in the direction of the arrow 100. The rotation of the control element 64 in turn is translated into an axial shifting of the pin 84 in the recess 82 of the control element 64 and therefore into an axial movement of the force transmission element 18 as indicated by the arrow 104.

As can be taken from FIGS. 4 and 5, the force transmission ratio is not changed by the different angular position of the handle 20 with respect to the shaft 12, because the lever arm a) and the lever arm b) have the same length as they do in the operation position shown in FIG. 4. Therefore, the movable grip element 22 need not be actuated with a different force in the two conditions shown in FIGS. 4 and 5, in order to actuate the movable tool 16, for example for removing tissue.

In addition, the instrument 10 of FIG. 1 can be disassembled into the handle 20, the tubular shaft 12 and the force transmission element 18. The releasable connection between the shaft 12 and the handle 20 as well as between the force transmission element 18 and the handle 20 have been described above. Further however, the force transmission element 18 can be removed from the shaft 12 by releasably connecting these parts by means of a bayonet connector in the region of the tools 14, 16.

Although the force translation element 18 in the above embodiment operates under compression, the force transmission mechanism of the present invention can be slightly modified. The guide slot of the recess 82 in the control element 64 can be oriented oppositely to the above configuration and thus easily adapted such that the force transmission element 18 operates under tension. In a similar manner, the force transmission from the movable grip element 22 to, the control element 64 can be replaced by a slight modification to be accomplished by actuating the coupling rod 76 under tension instead of compression.

In addition, the present invention can also be employed advantageously with scissor-like handles.

What is claimed is:

1. A handle for a medical instrument having a tubular shaft, comprising:
   at least one movable first grip element for being connected to a force transmission element axially movable in direction of a longitudinal axis of said tubular shaft to transfer motion of said at least one first movable grip element into an axial motion of said force transmission element,
   a second grip element,
   a coupling portion for connecting said tubular shaft with said handle,
   said coupling portion being pivotable and lockable relative to a handle axis about a pivot axis running transversely to said longitudinal axis of said tubular shaft, said coupling portion being connected to said second grip element, and said at least one movable first grip element being connected to said second grip element so that a relative position between said first grip element and said second grip element is unchanged upon pivoting said coupling portion relative to said handle axis,
   a control element formed as a double-arm lever, a first lever arm of which being connected to said at least one movable grip element, and a second lever arm of which being connected to said force transmission element, such that motion of said first movable grip element causes a rotation of said control element, wherein said control element translates said rotation into an axial movement of said force transmission element.

2. The handle of claim 1, wherein said pivot axis of said coupling portion coincides with a pivot axis of said control element.

3. The handle of claim 1, wherein said control element is connected to said coupling portion and rotates with said coupling portion when pivoted to form an angle with said handle with respect to said tubular shaft, wherein said connection between said first movable grip element for rotating said control element is releasable and can be re-established after rotation.

4. The handle of claim 1, wherein said at least one first movable grip element is connected to a first lever arm of a further double-arm lever, whose second lever arm is connected to said second lever arm of said control element, wherein a pivot axis of said further lever coincides with said pivot axis of said coupling portion.

5. The handle of claim 4, wherein said second lever arm of said further lever is connected via a pin to said control element, and wherein several holes are provided in said control element arranged on a partial circular section thereof, through which said pin is engageable depending on the pivot position of said coupling portion.

6. The handle of claim 1, wherein said coupling portion is pivotable in a total angular region of up to about 240° and is lockable in several pivot positions in said angular region by means of a locking mechanism.

7. The handle of claim 6, wherein said locking mechanism comprises a locking nose engageable with one of several recesses of said coupling portion, wherein said locking mechanism further comprises a button, so that by depressing said button said locking nose is disengageable with said respective recess.

8. The handle of claim 1, wherein said at least one movable grip element is connected to a first lever arm of a further double-arm lever and said second lever arm of said further lever is connected via a pin to said control element, and wherein several holes are provided in said control element arranged on a partial circular section thereof, through which said pin is engageable depending on the pivot position of said coupling portion which is lockable by means of a locking mechanism, and wherein said locking mechanism comprises a locking nose engageable with one of several recesses of said coupling portion, wherein said locking mechanism further comprises a button, so that by depressing said button said locking nose is disengageable with said respective recess, and wherein said pin is connected to said button and is disengageable with said respective hole by depressing said button.

9. The handle of claim 1, wherein said second lever arm of said control element comprises a recess formed as a guide slot in which a pin connected to or connectable to said force transmission element is axially guided.

10. The handle of claim 1, wherein said force transmission element is connected to said control element through a further lever.

11. The handle of claim 9, wherein said coupling portion comprises a receiving element for a proximal end of said force transmission element and wherein said receiving element is axially movable and is connected to said pin.

12. The handle of claim 11, wherein said receiving element comprises a locking mechanism for releasable connection of said force transmission element to said coupling portion.

13. The handle of claim 1, wherein said coupling portion comprises a receiving element for said tubular shaft for releasable connection of said tubular shaft to said coupling portion.

14. A medical instrument having a tubular shaft, comprising:
   at least one movable grip element for being connected to a force transmission element axially movable in direction of a longitudinal axis of said tubular shaft to transfer motion of said at least one movable grip element into an axial motion of said force transmission element,
   a coupling portion for connecting said tubular shaft with said handle,
   said coupling portion being pivotable and lockable relative to a handle axis about a pivot axis running transversely to said longitudinal axis of said tubular shaft,
   a control element formed as a double-arm lever, a first lever arm of which being connected to said at least one movable grip element, and a second lever arm of which being connected to said force transmission element, such that motion of said movable grip element causes a rotation of said control element, wherein said control element translates said rotation into an axial movement of said force transmission element,
   wherein said at least one movable grip element is connected to a first lever arm of a further double-arm lever, whose second lever arm is connected to said second lever arm of said control element, wherein a pivot axis of said further lever coincides with said pivot axis of said coupling portion.

15. The medical instrument of claim 14, wherein said second lever arm of said further lever is connected via a pin to said control element, and wherein several holes are provided in said control element arranged on a partial circular section thereof, through which said pin is engageable depending on the pivot position of said coupling portion.

16. A medical instrument having a tubular shaft, comprising:
   at least one movable grip element for being connected to a force transmission element axially movable in direction of a longitudinal axis of said tubular shaft to transfer motion of said at least one movable grip element into an axial motion of said force transmission element,
   a coupling portion for connecting said tubular shaft with said handle,
   said coupling portion being pivotable and lockable relative to a handle axis about a pivot axis running transversely to said longitudinal axis of said tubular shaft,
   a control element formed as a double-arm lever, a first lever arm of which being connected to said at least one movable grip element, and a second lever arm of which being connected to said force transmission element, such that motion of said movable grip element causes a rotation of said control element, wherein said control element translates said rotation into an axial movement of said force transmission element,
   wherein said second lever arm of said control element comprises a recess formed as a guide slot in which a pin connected to or connectable to said force transmission element is axially guided.

17. A medical instrument having a tubular shaft, comprising:
   at least one movable grip element for being connected to a force transmission element axially movable in direction of a longitudinal axis of said tubular shaft to transfer motion of said at least one movable grip element into an axial motion of said force transmission element,
   a coupling portion for connecting said tubular shaft with said handle,
   said coupling portion being pivotably and lockable relative to a handle axis about a pivot axis running transversely to said longitudinal axis of said tubular shaft,
   a control element formed as a double-arm lever, a first lever arm of which being connected to said at least one movable grip element, and a second lever arm of which being connected to said force transmission element, such that motion of said movable grip element causes a rotation of said control element, wherein said control element translates said rotation into an axial movement of said force transmission element,
   wherein said coupling portion comprises a receiving element for said tubular shaft for releasable connection of said tubular shaft to said coupling portion.

* * * * *